United States Patent [19]

Huang

[11] 4,439,182
[45] Mar. 27, 1984

[54] VALVULAR INFUSION DEVICE

[76] Inventor: Shing S. J. Huang, 521 Cape May St., Englewood, N.J. 07631

[21] Appl. No.: 357,854

[22] Filed: Mar. 15, 1982

[51] Int. Cl.³ ............................................. A61M 5/00
[52] U.S. Cl. .................................... 604/85; 604/247; 604/256
[58] Field of Search ............... 137/528, 533; 222/129, 222/145; 604/80, 81, 82, 83, 85, 89, 90, 246, 247, 256; 128/673, 674, 675

[56] References Cited

U.S. PATENT DOCUMENTS

| 3,416,567 | 12/1968 | Von Dardel | 137/604 |
| 3,861,388 | 1/1975 | Vaughn | 128/214 |
| 3,994,293 | 11/1976 | Ferro | 128/214 |
| 4,005,710 | 2/1977 | Zeddies | 128/214 |
| 4,257,416 | 3/1981 | Prager | 128/214 |

FOREIGN PATENT DOCUMENTS 737249  6/1966  Canada ................................. 128/46

OTHER PUBLICATIONS

Jansen, G. A., *Anesthesiology*, "A New Six-Way Stopcock", Feb. 1975, pp. 206-207.

*Primary Examiner*—Edward M. Coven
*Attorney, Agent, or Firm*—Anthony G. Eggink

[57] ABSTRACT

The valvular infusion device is for the administration of drugs or supplemental fluids into a parenteral fluid stream for intravenous infusion to a patient. The device includes a main conduit for generally the continual flow therethrough of a parenteral fluid, and at least one second conduit in communication with the main conduit to permit the injecting of drugs or supplemental fluids thereinto for transport with the parenteral fluid to a patient. The second conduits have valve chambers and compressible, resilient valve means therein, to permit only one-way flow of the drugs or supplemental fluids into the main conduit. The second conduits are provided with syringe receiving and securing means to provide a source for activating the pressure sensitive valve means and the injection of the required drugs or supplemented fluids for a patient. Additionally provided is a valvular infusion device for the induction of general anesthesia, which permits the injection of drugs utilizing only one hand of a user. And, provided are valve chamber and valve means for use therewith which minimize the volumetric "dead space" of the devices so as to facilitate the accurate injection of drugs or supplemental fluids. The infusion devices are, additionally, designed for disposable, one-time use, and for use with commonly known intravenous administration apparatus.

17 Claims, 7 Drawing Figures

VALVULAR INFUSION DEVICE

This invention relates to a device for use in the parenteral administration of fluids to a patient. Particularly, this invention relates to a valvular infusion device which permits a physician or user, utilizing one hand, to accurately inject drugs or secondary, supplemental fluids into a primary, parenteral fluid stream for intravenous infusion into a patient.

Several types or configurations of infusion devices for medical use have heretofore been proposed or utilized. These devices have either been complex in design, expensive to manufacture, limited or restricted in use, required two-hand operation, or have resulted in the inaccurate injection of drugs or supplemental fluids into a parenteral fluid stream due to the design of the device.

For example, one such prior art configuration requires the penetration of syringe needles into a resealable block or membrane for the introduction of supplemental fluids into a parenteral fluid stream. However, this puncturing process introduces the risk of contaminating the parenteral fluid stream with particles from the block or membrane material which may subsequently enter the body of a patient. Another device configuration uses a stopcock design which requires a physician or user to utilize both hands to initiate the flow of a drug or supplemental fluid from a syringe into the parenteral fluid stream. Other device configurations result in the inaccurate dispensing of drugs or supplemental fluids into a parenteral fluid stream due to excessive volumetric "dead spaces" inherent in the respective infusion devices. And, the latter difficulty is often exasperated due to the relatively small volumes of drugs or supplemental fluids required and injected for medical purposes, particularly in the administration of general anesthesia. Additionally, other infusion devices either restrict the injection into a parenteral stream to one drug or supplemental fluid, or present a potentially undesirable situation when two or more drugs or supplemental fluids are injected. With respect to the latter, should the injected drugs or fluids be incompatible, their mixing could render an undesired chemical reaction or could result in a coagulated mixture which would hinder further infusion.

Infusion devices according to this invention overcome the problems and difficulties of those devices discussed above. The infusion devices according to the invention are useful to provide to a physician or user a fast, reliable, inexpensive, accurate and one-handed means to inject drugs or supplemental fluids into a primary, parenteral fluid stream for infusion into a patient. The infusion devices are especially useful during the induction of general anesthesia, when, for example, an intravenous anesthetic, such as thiopental sodium, and a depolarizing agent, such as succinylcholine chloride, are separately injected into an intravenous solution for administration to a patient. The ability of the anesthesiologist to administer drugs or supplemental fluids utilizing one hand permits the other hand free to check and adjust instruments, the placement of the oxygen mask on the face of the patient, etc.

The infusion devices according to the invention provide one-way valve means which permit a plurality of drugs or supplemental fluids, without mixing, to be injected into a primary parenteral fluid stream for transport to a patient. The devices provide means to receive syringes for the accurate injection of these drugs or supplemental fluids, and are adaptable to be communicatively connected to other commonly utilized intravenous-type medical apparatus. Additionally, the configuration of the one way valve means to the parenteral fluid stream flow is to minimize the volumetric "dead space" of the devices.

Despite the longstanding need for an accurate, effective and easy to utilize infusion device for the administration of a plurality of fluids intravenously to a patient, none in so far as is known has been developed. An effective, accurate and multi-purpose valvular infusion device adaptable to receive one or more syringes, and which is easily manipulated with one hand by a user to administer one or more drugs or fluids, without mixing, intravenously to a patient, is provided by the teachings of this invention.

In summary, this invention provides an infusion device having one-way valve means for the administration of drugs or supplemental fluids into a primary, parenteral fluid for intravenous infusion to a patient. The device includes a main tubular conduit for the continuous flow therethrough of a primary, parenteral fluid or solution. The main conduit is generally an elongated, walled structure having an inlet end and an outlet end for communicative connection to other such devices or to commonly utilized intravenous administration apparatus. Intermediate the opposing ends of the main conduit is at least one aperture or opening extending through the walled structure for receiving drugs or supplemental fluids therethrough. A second tubular conduit extends outwardly from the exterior wall of the main conduit about each of the apertures or openings in the walled structure. At the outward end of the second conduit are means for receiving and securing the tip or end of a syringe. Intermediate the outward end of the second conduit and the apertured exterior wall of the main conduit is a stricture extending inwardly from the interior surface of the second conduit. A valve cavity or valve chamber is defined in the interior of the second conduit between the stricture and the exterior of the wall of the main conduit.

A compressible and resilient valve means having generally the configuration of the valve cavity is securedly placed therein. The valve means has an apex portion for abutment against the stricture within the second conduit to seal the opening remaining. The valve means provides for the one-way passage of fluids from the outward or inlet end of the second conduit through the valve chamber or cavity and into the main conduit through the aperture of the main conduit wall. The compressible and resilient valve means responds to an externally pressurized drug or fluid to permit one-way flow through the valve cavity.

In use, the valvular infusion device is communicatively connected at the inlet end of the main tubular conduit to a parenteral fluid source. And, by means of flexible tubing and a venipuncture needle, the outlet end of the device's main conduit is communicatively connected to a vein of a patient to generally permit the continuous flow of parenteral fluid to the patient.

When a drug or supplemental fluid is required for intravenous infusion to a patient, a syringe containing that drug or fluid is communicatively and securely connected to the syringe receiving means at the outwardly extending or inlet end of the second tubular conduit of the infusion device. Any number of such drug containing syringes can be so situated in that a plurality of second conduit members can extend from the main conduit body. The suppression of a syringe plunger causes the drug or fluid, under pressure, to force the apex of the valve means from the stricture within the second conduit by compressing the valve means, and, thus, permits the drug or fluid to pass through the valve cavity through the main conduit wall aperture and into the parenteral fluid stream for passage to the patient. Discontinuation of pressure on the syringe plunger causes the resilient character of the valve means to reseal the stricture in the second conduit. Additionally, the resilient nature of the valve means prevents the fluid stream in the main conduit from entering the second conduit beyond the bottom portion of the valve means. Particularly, the valve means prevents a drug or supplemental fluid injected from one syringe attached to the infusion device from mixing with a drug or fluid in another syringe attached to the device.

Also provided by the invention are devices having main conduit diameter dimensions of predetermined size, whereby the inlet and outlet end portions the devices are frictionally interlockable with other such devices, and are adaptable to receive standard intravenous administration apparatus.

Additionally provided by the invention is a device having two secondary valvular conduits in communication with a single primary conduit. This device is particularly suited for use in the area of anesthesia, and permits an anesthesiologist during the induction of general anesthesia to inject drugs and supplemental fluids into a parenteral fluid stream with accuracy and utilizing only one hand, and, importantly, freeing the use of the opposite hand for other necessary purposes.

And, provided by the invention are devices having valve configurations for use therewith which when placed in the valve cavities adjoining the apertured wall of the main conduits provide a minimal "dead space" volume. Also, provided are devices constructed of materials which provide devices suitable for one-time use, disposable purposes.

These and other benefits of this invention will become clear from the following description by reference to the drawings, wherein.

Figure 1:
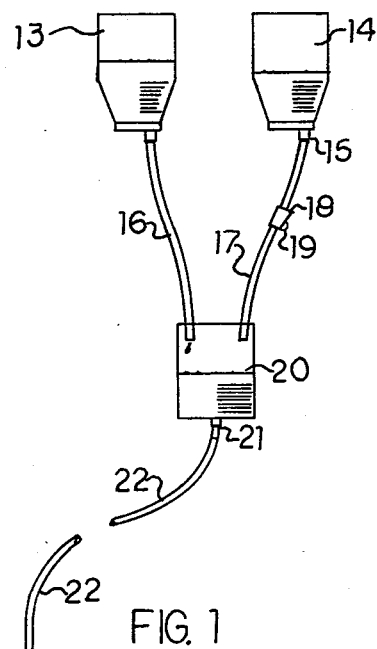
FIG. 1 is a diagrammatic view of an intravenous administration assembly including a parenteral fluid source and a syringe containing a drug or supplemental fluid connected to an infusion device of this invention.

Referring to FIG. 1, a commonly utilized intravenous administration assembly is there illustrated. A valvular infusion device 40 of this invention is shown communicatively incorporated for use with the commonly known and utilized intravenous administration assembly apparatus. The infusion device 40 has a main tubular conduit 41 and second tubular conduit members 49 and 50. The second conduits 49 and 50 are utilized to receive a supplemental fluid or drug, as for example, from a syringe 26, so that a predetermined volume of fluid or drug contained in the syringe 26 can be injected, as required, into the generally continual fluid stream passing through main conduit 41. The valvular infusion device embodiment 40, shown in FIG. 1, having two second conduit members 49 and 50 is particularly useful for the induction of general anesthesia in that two fluids or drugs are often required for administration to a patient with the parenteral fluid stream.

The administration assembly, as shown in FIG. 1, generally consists of parenteral fluid sources 13 and 14. These sources are generally inverted containers filled with either blood or solutions of glucose or electrolytes. Flexible tubing 16 and 17 extend communicatively downward from the containers, and are generally frictionally fit over a container extension 15. When required, a tube clamping device 18, having a pinching, rotatable member 19, is used on any flexible tubing portion of the assembly to ensure the prevention of fluid flow through, or from, various portions of the assembly. The flexible tubes 16 and 17 enter a drip chamber 20. A flexible tube 22 frictionally fit to a drip chamber extension 21 is communicatively connected to the inlet end 42 of valvular infusion device 40. Finally, from the outlet end 43 of device 40, a flexible tube 24 extends to a cannula 25 which is inserted into a vein of a patient.

In normal operation, the intravenous administration assembly permits a generally continual flow of a parenteral fluid, or a combination of fluids or solutions, such as, blood, glucose, electrolytes, etc., to be intravenously administered to a patient. The addition of the valvular infusion device 40 of this invention to this intravenous administration assembly does not interfere with this process. However, when a drug or supplemental fluid, such as an anesthetic agent is required for administration, it is only necessary for an anesthesiologist to suppress plunger 28 of syringe 26, which contains the required drug or fluid, to effectuate the transfer of the desired quantity or volume of the drug or fluid into the parenteral fluid stream for flow therewith into the vein of a patient.

Figure 2:
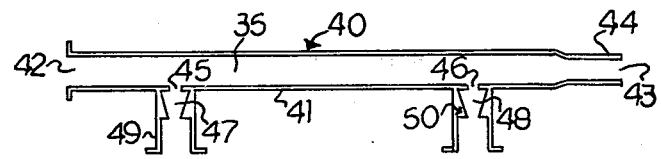
FIG. 2 is a schematic, longitudinal cross section of the device embodiment shown in FIG. 1, which embodiment is well suited for the administration of general anesthesia.

As mentioned above, the infusion device embodiment shown in FIG. 1, and in more detail in FIG. 2, is particularly suited for the induction of general anesthesia. The device 40 has a primary tubular conduit 35 having an inlet end 42, an outlet end 43 and a wall structure 41. The wall structure 41 has two apertures 45 and 46 extending therethrough, and two outwardly extending second conduits 49 and 50. Within the respective second conduits 49 and 50 are valve cavities or chambers 47 and 48, which are suitable to receive valve means, which permit one-way flow and which will be described below. Additionally, device 40 has a telescoping outlet tip 44 designed to either frictionally fit into the inlet ends of similar infusion devices, or to fit into other intravenous administration assembly components, such as tubing, or the like. Device embodiment 40 generally provides for the securement of two syringes, or, alternatively, one syringe and a flexible tube having a pressurized supplemental fluid source therein. Thus, a device according to the teachings of the invention can provide for the injection of any number of supplemental fluids or drugs, at any point of the length of a single main conduit member.

The particular embodiment illustrated in FIGS. 1 and 2, provide an anesthesiologist with many advantages. First, once a pair of syringes are secured to the second conduit members 49 and 50, the device 40, with drug or fluid containing syringes communicatively attached, can be placed on a table or flat surface, so that a one-handed suppression of the syringe plunger can introduce into the parenteral fluid stream the required quantity or volume of drugs or fluids. This enables the anesthesiologist to utilize the other free hand for other vital purposes, such as, ensuring the proper placement of an oxygen mask on the face of a patient, adjusting instruments, etc. Additionally, a drug or fluid injected through valve chamber 47, for example, and into the main conduit 35 is prevented from flowing through aperture 46, through valve cavity 48 and into the syringe attached at the inlet portion of conduit 50. This flow is prevented due to the inherent nature of the one-way valves utilized in these devices, as will be discussed below. However, the prevention of this flow is important because of the danger in mixing incompatible drugs or fluids, which can coagulate or react chemically to the detriment of the infusion assembly function, and, obviously to the effect on the patient. As discussed above, this possibility exists particularly in the administration of anesthetic drugs and related fluids. Also, because the quantities or volumes of anesthetic drugs or fluids are often relatively small, it is important that a minimal "dead space" volume be maintained in the design and configuration of the apparatus utilized in the administration of these drugs or fluids. As will be shown, the valve cavities of the devices of this invention, in conjunction with the valve means utilized, reduce this difficulty so that accurate volumes of drugs and fluids are in fact administered.

Figure 4:
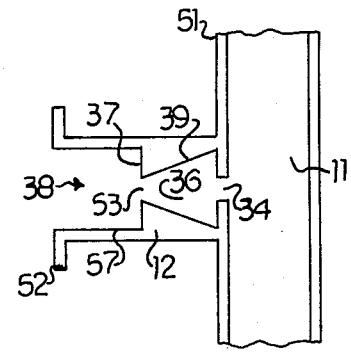
FIG. 4 is a cut-away, schematic cross sectional view showing the communication between the main and second conduits of the infusion device of this invention, and which, particularly, shows the valve chamber thereof.
Figure 7:
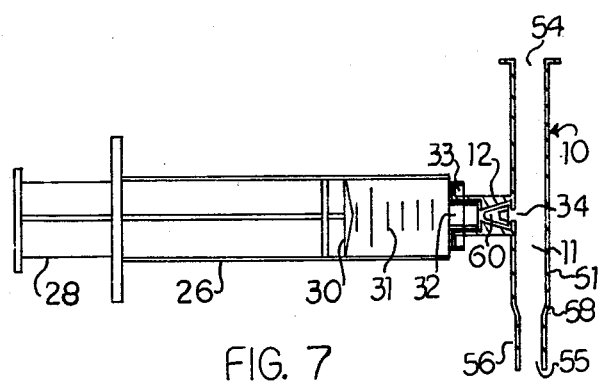
FIG. 7 is a schematic cross sectional view of a syringe secured to the inlet portion of the second conduit of a valvular infusion device of this invention.

FIG. 4 is an expanded view of the intersection of a main conduit 11 and a second conduit 12. This view illustrates generally the configuration of the valve chamber or cavity 36, which is similar in configuration irrespective of the number of second conduit members which extend from the primary conduit, for example, two second conduits as shown in FIG. 2, or a single second conduit as shown in FIG. 7. The second conduit 12 extends outwardly from the wall structure 51 of the primary conduit 11, and the walled structure of the second conduit 12 is congrous with wall 51. The second conduit 12 is disposed about or around the aperture 34 of wall 51 so that it communicates with main conduit 11. The second conduit 12 has an inlet portion 38 and an outlet portion at and near aperture 34. Intermediate the length of the second conduit 12 or between the inlet portion 38 thereof and the exterior surface of wall 51 of main conduit 11 is a stricture 37. The stricture 37 extends inwardly from the interior wall 57 of the second conduit, and it has an opening 53 which permits communication between the inlet portion 38 and the valve cavity 36 of second conduit 12. A telescoping side wall surface 39 which extends from the opened stricture 37 to wall structure 51 further defines the valve cavity 36. As will be discussed further below, the actual configuration of valve cavity or chamber 36 can vary depending upon the valve means configuration used in conjunction therewith.

Also shown in FIG. 4 is a syringe receiving means or portion at the inlet portion of the second conduit. A generally walled and circular in cross section inlet portion is suitable for frictionally receiving the needle-less tip of a common syringe so that the tip of the syringe itself abuts the inwardly extending wall of stricture 37. Preferably, a syringe securing means 52 is disposed at the inlet portion, and which acts in conjunction with the syringe receiving means to hold a syringe in place with the infusion device. The syringe securing means 52 is shown as a circumferential lip portion at the inlet portion 38 of second conduit 12. This lip portion serves as a male threading structure for rotating into the internally threaded extension member 33 of syringe 26, as shown in FIG. 7. Thus, the walled inlet portion 38, having a configuration or predetermined inside diameter to preferentially permit the frictional fit of a syringe tip 32 therein, and which results with syringe tip 32 against the generally flat exterior surface of the opening 53 of stricture 37 as the syringe is rotated onto securing means 52, provides an arrangement that permits a drug or supplemental fluid to be injected through opening 53 as plunger 28 is suppressed in the attached syringe 26.

To further clarify the infusion device of this invention, FIG. 7 illustrates a valvular infusion device 10 having a syringe 26 attached and secured to its second conduit 12. The device 10 is further shown to have an inlet end 54, an outlet end 55 and a wall structure 51. The aperture 34 in wall structure 51 permits the communicative connection between the second tubular conduit 12 and the primary conduit 11, and a valve means 60 is shown in the second conduit 12 directly adjacent the aperture 34. As further illustrated, the outlet end 55 has a telescoping outlet tip 56 which has generally an outside diameter that permits frictional fitting or locking into the internal circumferential surface of an inlet end 54 of a similar infusion device. The syringe 26 shown attached to second tubular conduit 12 is of the type having a plunger 28, a piston 30, volumetric markings or gradations 31, an exit tip 32 and an internally threaded extension member 33. Syringes such as these are commonly utilized for medical purposes, and their dimensions, particularly at the tip, are generally uniform.

Figure 5:
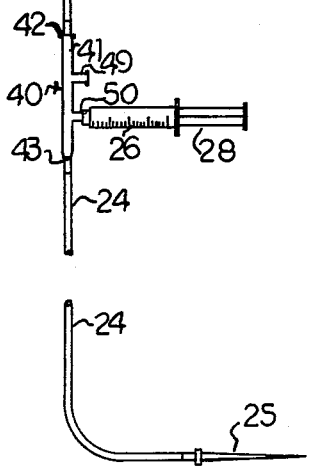
FIG. 5 is a schematic side view of a valve means for use in the infusion devices of this invention.
Figure 5:
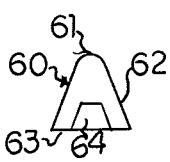
Figure 6:
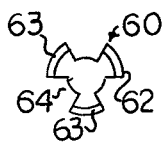
FIG. 6 is a schematic bottom view of the valve means shown in FIG. 5.

FIGS. 5 and 6 illustrate an embodiment of a compressible and resilient valve means 60 for use in valve cavity 36 to permit only one-way flow of supplemental fluids or drugs from a second conduit 12 into a primary conduit 11, as shown in FIG. 4. Valve means 60 consists of an apex 61 which when normally placed, without external pressure, within valve cavity 36 abuts against opening 53 of stricture 37 to, thereby, seal opening 53. The valve 60 increases in diameter from apex 61 and has a side surface 62 and generally a bottom surface structure 63. As illustrated, three legs extend downward beginning at a point intermediate the apex 61 and bottom 63. The existence of these leg portions, define a number of channel or groove openings 64. However, the actual number of legs and corresponding channels or openings into the valve body can vary depending upon a number of factors that are important to the function of the valve itself.

The valve means 60 fits into the valve chamber or cavity to permit one-way flow of a fluid from the inlet portion of the second conduit into the primary conduit. The valve means 61 is preferably positioned in the valve cavity with the valve apex 61 being disposed against opening 53 of stricture 37 while its bottom surface 63 is disposed against the exterior of wall surface 51 within the valve cavity 36. Thus, without external forces the valve apex rests against the opening 53. However, the overall length of the valve body relative to the length of the valve cavity, the compressive strength of the valve material, and the pressure exerted on the valve through aperture 34 (peripheral vein pressure of the patient and the pressure of the parenteral fluid due generally to gravitational force) all contribute to the force abutting the valve apex against opening 53.

The above identified pressure factors all contribute to the self-sealing character of the one-way valve 60. However, it is preferred that an external pressure of 10 to 15 cm. of $H_2O$ exerted on the valve through the inlet portion of the second conduit will cause a drug or fluid to compress or move the apex of the valve from opening 53 to permit passage of the drug or fluid. This pressure as noted above is usually exerted by means of a syringe attached to the second conduit. However, it is also possible to attach a tube at the second conduit inlet portion, whereby a fluid from a bottle having the necessary pressure is continually or when necessary, injected through the second conduit and into the main conduit fluid stream.

It is also preferred that the configuration of valve means 60 consumes the volume within valve cavity 36 as much as possible so that the volumetric "dead space" is kept to a minimum. Thus, it is preferred that the configuration of the valve means is generally similar to that of the valve cavity in which it is placed. As shown in the drawings, the valve bodies are generally conical in configuration, as are the valve cavities or chambers within the second conduit members of the infusion devices. However, for purposes of this invention, the valve means need only be compressible and resilient in nature, irrespective of configuration. The valve means are importantly one-way flow responsive.

The valve means 60 can be constructed of any suitable compressible and resilient material, such as a rubber, plastic or a polymeric material. The material should, however, be chemically inert to the drugs, supplemental and parenteral fluids with which it comes in contact. Additionally, the material should be non-absorbant in nature. The valve means can be molded of one material or constructed of several materials; for example, one compressible and resilient material portion for use as the upper apex, and a more rigid material portion for use as leg members, which define the channel or grooved portions in the valve.

Figure 3:
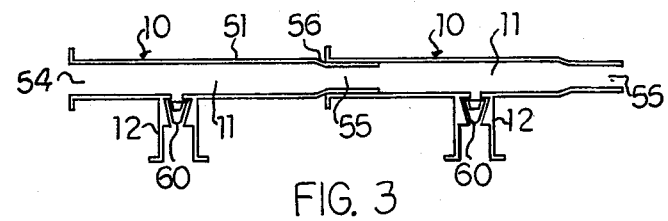
FIG. 3 is a schematic, longitudinal cross section of a pair of frictionally interlocked valvular infusion devices of the invention, wherein each device has one second valvular conduit in communication with a main conduit.

Before discussing the material construction of the infusion device body of the invention, FIG. 3 is described. There illustrated, are two frictionally interlocked valvular infusion devices 10. Each device member 10 has a single second conduit 12 extending therefrom, and this conduit 12 has been discussed, particularly, with reference to FIG. 4. The telescoping outlet tip 56 of one device 10 is shown inserted into the inlet end of the second device. Although the device embodiment illustrated in FIGS. 1 and 2 is preferred for purposes of induction of general anesthesia, an interlocked device arrangement could, alternatively, be utilized. Additionally, the administration of any number of drugs or supplemental fluids into a primary fluid stream can be effectuated in this manner.

The device bodies of this invention can be inexpensively manufactured of a thermoplastic or similar material suitable for use in an injection molded process. The resulting thermoplastic devices would be suitable for one-time, disposable use.

The valvular infusion device of this invention can obviously be manufactured to meet any desired size requirement. However, for use in conjunction with other intravenous assembly apparatus, it has been found that a device body having a single second conduit, is well suited having a length of about 30 mm., an inside diameter inlet end of about 4 mm., an outside diameter for the telescoping outlet end tip of about 3.8 mm., and about a 4 mm. inside diameter inlet portion for the second tubular conduit. For the device having essentially a pair of second conduit members, the dimensions are generally the same, except for the device body length, which is approximately 93 mm. Additionally, because this latter device is designed for anesthesia induction purposes, which generally requires the securement to the second conduit members of two syringes, for example, a 50 cc. and a 20 cc. syringe, the distance between the second conduit members is approximately 43 mm.

The actual wall thickness for the above mentioned devices would obviously depend upon materials utilized, the pressure requirements for the device, and the size of the device. If, for example, a 1 mm. wall thickness is utilized, it would be possible to increase that wall thickness at specific critical portions of the device body. For example, a device specifically designed for anesthesia induction purposes, may have a reinforced, or thicker wall main conduit intermediate the two second conduit members. However, the actual dimensions described above are merely illustrative for purposes of further illuminating the teachings of this invention.

As many changes are possible to the embodiments of this invention, utilizing the teachings of the invention, the description above, and the accompanying drawings, should be interpreted in the illustrative, and not in the limited sense.

That which is claimed is:

1. A valvular infusion device for the administration of a parenteral fluid and at least one supplemental fluid or drug for intravenous infusion to a patient, said valvular infusion device having non-movable valve means positioned in a valve chamber for the one-way flow of the supplemental fluid into the parenteral fluid stream, said device comprising:
  a. a main conduit for generally the continual flow therethrough of a parenteral fluid, said main conduit being generally an elongated, walled passage having an interior and an exterior wall surface, an inlet end and an outlet end, said main conduit further having at least one aperture which extends through said passage wall from said interior to said exterior wall surface and which is disposed between said inlet end and said outlet end of said conduit,
  b. at least one second conduit extending from and being in communication with said main conduit for receiving and the flow therethrough of a supplemental fluid or drug, said second conduit being a walled passage having an inlet portion, an outlet portion and an inwardly extending stricture therebetween, said outlet portion of said second conduit extending generally outwardly from and congruous with said main conduit and being disposed about said aperture in said main conduit,
  c. a valve chamber in said second conduit for receiving a non-movable, one-way valve therein, said chamber being disposed at said outlet end of said second conduit in adjacent proximity and about said aperture of said main conduit said valve chamber being generally defined by the exterior surface of said wall structure about said aperture of said main conduit exposed within said second conduit and said inwardly extending stricture within said second conduit, and, d. a non-movable, compressible and resilient valve means for permitting one-way flow of a supplemental fluid or drug from said inlet portion of said second conduit through said valve chamber and through said aperture in said main conduit wall and into said main conduit, said valve means being located in said valve chamber in a sealing, contact configuration with said second conduit stricture and said exterior wall structure surface of said main conduit disposed within said valve chamber, whereby, a supplemental fluid or drug under pressure introduced into said inlet portion of said second conduit interrupts said sealing contact of said valve means by compressing said valve means into itself in said valve cavity, and to, thereby, permit the passage of the supplemental fluid or drug, between the cavity walls and the valve means by compressing it, and through said main conduit wall aperture for transfer with the parenteral fluid into the vein of a patient, and, whereby, subsequent to the release of the pressure of the supplemental fluid said compressible and resilient valve reseals said stricture in said second conduit.

2. The valvular infusion device of claim 1, wherein, said second conduit of said device additionally has syringe receiving means disposed at said inlet portion, said syringe receiving means for receiving the needle-less end portion of a syringe in a frictional manner, whereby, a syringe containing a drug or fluid can be frictionally received by said second conduit inlet portion, and utilized to introduce a drug or fluid, under pressure, thereinto.

3. The valvular infusion device of claim 1, wherein said inlet portion of said second conduit additionally has syringe securement means for securing a syringe in communication therewith, said securement means comprised of a circumferential lip portion extending outward from said inlet portion of said second conduit to permit the threaded securement thereonto of an internally threaded needle-less syringe tip.

4. The valvular infusion device of claim 1, wherein, said main conduit, said at least one second conduit and said valve chamber is constructed of a one-piece, injection molded, thermoplastic material for disposable, one-time use purposes.

5. The valvular infusion device of claim 1, wherein, said main conduit is generally an elongated, tubular structure having generally a circular cross section, and, wherein, said main conduit has generally a telescoped outlet end having an outside diameter suitable for frictional insertion into the inside of an inlet end of a similar device, whereby, said device fitted end to end with similar devices permit the infusion of a plurality of supplemental fluids or drugs into a parenteral fluid stream.

6. The valvular infusion device of claim 1, wherein, said valve chamber of said device consists of a generally conically tapered cavity which extends from the inwardly extending stricture of said conduit to said exterior surface of said main conduit wall about said aperture therein disposed within said second conduit.

7. The valvular infusion device of claim 5, wherein, said compressible and resilient valve means is constructed of a generally fluid impermeable and medically inert plastic or rubber material, said valve means further having a generally conically tapered configuration for generally the frictional fitting within said valve chamber, said valve means further having an upper apex portion for abutment against said inwardly extending stricture of said second conduit and having a plurality of leg members for abutment against the exterior surface of said main conduit disposed within said second conduit about said aperture of said main conduit, said plurality of leg members of said valve means having channel means therebetween to permit the passage of fluid, whereby, said valve means permits the one-way passage of a supplemental fluid or drug as a fluid or drug is introduced, under pressure, against said valve apex, and whereby, the disposition of said valve means within said valve chamber provides for a minimal "dead space" volume so as to provide for the accurate administration of a supplemental fluid or drug to a patient.

8. The valvular infusion device of claim 1, wherein, said valve means responds in compressibility to an external pressure range of 10 to 15 cm. of $H_2O$.

9. A valvular infusion device for the induction of general anesthesia, said device having a main conduit with a second and a third conduit extending outwardly therefrom to permit the one-handed infusion of two drugs or supplemental fluids into a primary, parenteral fluid stream for administration intravenously to a patient, said device further having a valve chamber disposed at one end of the second and third conduit for receiving a non-movable valve therein and having syringe securing means disposed at the opposite ends of the second and third conduits to permit the secured attachment of a syringe in communication therewith, said device comprising:

a. a main conduit for generally the continual flow therethrough of a parenteral fluid, said main conduit being a walled passage having an inlet end, an outlet end and two apertures in said wall, b. a second conduit in communication with one said apertures of said main conduit, said second conduit having an inlet portion, an outlet portion adjacent said aperture, and an inwardly extending stricture, c. a third conduit in communication with said other aperture in said main conduit, said third conduit having an inlet portion, an outlet portion adjacent said other aperture, and an inwardly extending stricture, d. two valve chambers, one said valve chamber disposed adjacent said main conduit at said outlet portion of said second conduit, and said other valve chamber disposed adjacent said main conduit at said outlet portion of said third conduit, each said valve chamber having an interior surface area, e. a non-movable, one-way valve means stationarily disposed in said valve chamber of said second conduit and in said valve chamber of said third conduit, said valve means being of a compressible and resilient construction and being in touching contact with the interior surface areas of each said valve chamber for minimizing the dead spaces therein to increase the volumetric accuracy of the supplemental fluids to be infused, and, f. syringe securement means disposed at the inlet portion of said second conduit and at the inlet portion of said third conduit, whereby, one supplemental fluid or drug containing syringe can be securedly attached to said syringe securement means of each said second and third conduit to, thereafter, permit the one-handed injection of two supplemental fluids or drugs into a single parenteral stream for intravenous infusion to a patient, and, whereby, the one-way valves prohibit the intermixing of the two drugs or fluids.

10. The valvular infusion device of claim 9, wherein, said valve members respond in compressibility to an external pressure range of 10 to 15 cm. of $H_2O$, and wherein said main conduit, said second conduit, said third conduit, and said valve chambers are constructed of a one-piece, injection molded, thermoplastic material for disposable, one-time use purposes.

11. The valvular infusion device of claim 9, wherein, said syringe securement means consist of circumferential lip portions extending outwardly from said inlet portion of said second conduit and said inlet portion of said third conduit to permit the threaded securement thereonto of internally threaded syringe tips.

12. The valvular infusion device of claim 9, wherein, said main conduit is generally an elongated, tubular structure having generally a circular cross section, said main conduit further having a telescoped outlet end having an outside diameter suitable for frictional insertion into the inside of an inlet end of a similar device.

13. The valvular infusion device of claim 9, wherein said second and third conduits are respectively for the infusion of an anesthetic fluid and a depolarizing agent.

14. A valvular infusion device for the injection of a secondary fluid into a primary fluid flowable therethrough, said device comprising a main conduit having an inlet, an outlet, and at least one other opening thereinto, a second conduit member extending outwardly from said main conduit and having an interial, walled passage for communication with each said other opening into said main conduit, a valve chamber defined by said interial, walled passage of said second conduit member adjacent each said other opening of said main conduit, and non-movable, one-way valve means disposed in each said valve chamber, said one-way valve means being pressure sensitive to permit secondary fluid flow only from said second conduit member through said opening and into said main conduit for flow with a primary fluid, said valve chamber further being a conically disposed interial space, and said valve means being collapsible, resilient and conical in construction for the non-movable and touching seating within said conically disposed interial space of said valve chamber to minimize the volumetric flow dead space therein for the accurate administration of secondary fluids.

15. A valvular infusion device of claim 14, wherein, said primary conduit essentially has two said other openings thereinto so as to permit the one-way flow of two secondary fluids only, said device particularly for use in the induction of general anesthesia.

16. The valvular infusion device of claim 14, wherein, each said second conduit member has syringe securement means to permit the communication of two syringes with said device, whereby, subsequent to the securement of two syringes the secondary fluids can be injected into a primary fluid by means of one-handed suppression of the syringe plungers.

17. The valvular infusion device of claim 14, wherein said main conduit is generally an elongated, tubular structure having generally a circular cross section, said main conduit further having a telescoped outlet end having an outside diameter suitable for frictional insertion into the inside of an inlet end of a similar device.

* * * * *